United States Patent
Norton et al.

(10) Patent No.: US 7,471,392 B2
(45) Date of Patent: Dec. 30, 2008

(54) POLARIMETRIC SCATTEROMETRY METHODS FOR CRITICAL DIMENSION MEASUREMENTS OF PERIODIC STRUCTURES

(75) Inventors: Adam E. Norton, Palo Alto, CA (US); Abdurrahman Sezginer, Los Gatos, CA (US); Fred E. Stanke, Cupertino, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 11/903,238

(22) Filed: Sep. 21, 2007

(65) Prior Publication Data

US 2008/0037015 A1  Feb. 14, 2008

Related U.S. Application Data

(63) Continuation of application No. 11/105,099, filed on Apr. 13, 2005, now Pat. No. 7,289,219, which is a continuation of application No. 10/857,223, filed on May 28, 2004, now Pat. No. 6,909,507, which is a continuation of application No. 10/112,138, filed on Mar. 29, 2002, now Pat. No. 6,778,273.

(60) Provisional application No. 60/280,714, filed on Mar. 30, 2001.

(51) Int. Cl.
*G01J 3/28* (2006.01)
(52) U.S. Cl. .................. 356/327; 356/445; 356/237.5
(58) Field of Classification Search ............... 356/327, 356/369, 445, 237.2–237.5
See application file for complete search history.

(56) References Cited

U.S. PATENT DOCUMENTS 3,858,983 A  1/1975  Foster et al. .................. 356/448
4,745,526 A  5/1988  Sestak .......................... 362/35

(Continued)

FOREIGN PATENT DOCUMENTS

EP  0 816 926  1/1998

(Continued)

OTHER PUBLICATIONS

"Automated Multiple Angle of Incidence Ellipsometer System," *IBM Technical Disclosure Bulletin*, vol. 32, No. 9A, Feb. 1990, pp. 417-424.

(Continued)

*Primary Examiner*—Kara E Geisel
(74) *Attorney, Agent, or Firm*—Stallman & Pollock LLP

(57) ABSTRACT

An optical measurement system for evaluating a sample has a motor-driven rotating mechanism coupled to an azimuthally rotatable measurement head, allowing the optics to rotate with respect to the sample. A polarimetric scatterometer, having optics directing a polarized illumination beam at non-normal incidence onto a periodic structure on a sample, can measure optical properties of the periodic structure. An E-O modulator in the illumination path can modulate the polarization. The head optics collect light reflected from the periodic structure and feed that light to a spectrometer for measurement. A beamsplitter in the collection path can ensure both S and P polarization from the sample are separately measured. The measurement head can be mounted for rotation of the plane of incidence to different azimuthal directions relative to the periodic structures. The instrument can be integrated within a wafer process tool in which wafers may be provided at arbitrary orientation.

20 Claims, 1 Drawing Sheet

U.S. PATENT DOCUMENTS

| | | | |
|---|---|---|---|
| 4,933,567 A | 6/1990 | Silva et al. | 356/369 |
| 5,042,951 A | 8/1991 | Gold et al. | 356/369 |
| 5,329,357 A | 7/1994 | Bernoux et al. | 356/369 |
| 5,394,247 A | 2/1995 | Vahey et al. | 356/429 |
| 5,432,607 A | 7/1995 | Taubenblatt | 356/364 |
| 5,608,526 A | 3/1997 | Piwonka-Corle et al. | 356/369 |
| 5,640,244 A | 6/1997 | Hellstrom et al. | 356/446 |
| 5,726,756 A | 3/1998 | Aki et al. | 356/237.2 |
| 5,801,824 A | 9/1998 | Henley | 356/237.2 |
| 5,818,061 A | 10/1998 | Stern et al. | 356/613 |
| 5,867,276 A | 2/1999 | McNeil et al. | 356/445 |
| 5,910,842 A | 6/1999 | Piwonka-Corle et al. | 356/369 |
| 5,995,218 A | 11/1999 | Ide | 356/237.1 |
| 6,032,071 A | 2/2000 | Binder | 356/369 |
| 6,038,026 A | 3/2000 | Maris | 356/514 |
| 6,052,191 A | 4/2000 | Brayden, Jr. et al. | 356/630 |
| 6,184,984 B1 | 2/2001 | Lee et al. | 356/369 |
| 6,297,880 B1 | 10/2001 | Rosencwaig et al. | 356/369 |
| 6,359,212 B1 | 3/2002 | Hall et al. | 356/239.2 |
| 6,362,881 B1 | 3/2002 | Pickering et al. | 356/369 |
| 6,423,977 B1 | 7/2002 | Hayasaki et al. | 356/237.5 |
| 6,473,186 B2 | 10/2002 | Kawasaki et al. | 356/512 |
| 6,493,064 B2 | 12/2002 | Cabiri et al. | 356/400 |
| 6,507,394 B1 | 1/2003 | Cheng et al. | 356/237.5 |
| 6,539,325 B1 | 3/2003 | Numata et al. | 702/127 |
| 6,563,586 B1 | 5/2003 | Stanke et al. | 356/445 |
| 6,611,330 B2 * | 8/2003 | Lee et al. | 356/369 |
| 6,721,052 B2 | 4/2004 | Zhao et al. | 356/369 |
| 6,842,250 B2 | 1/2005 | Schwarz | 356/445 |
| 2001/0033378 A1 * | 10/2001 | Rosencwaig et al. | 356/369 |
| 2002/0018217 A1 | 2/2002 | Weber-Grabau et al. | 356/601 |
| 2004/0207844 A1 * | 10/2004 | Nabatova-Gabain et al. | 356/369 |

FOREIGN PATENT DOCUMENTS

| | | |
|---|---|---|
| JP | 58034310 | 2/1983 |
| JP | 05060527 | 3/1993 |
| JP | 08190066 | 7/1996 |
| JP | 09138364 | 5/1997 |
| JP | 10300861 | 11/1998 |
| JP | 11295785 | 10/1999 |
| JP | 2001305071 | 10/2001 |
| WO | WO 99/02970 A1 | 1/1999 |
| WO | WO 00/02037 A1 | 1/2000 |

OTHER PUBLICATIONS

"Automated, Remote, Programmable, Ellipsometer Drive Mechanism," *IBM Technical Disclosure Bulletin*, vol. 31, No. 9, Feb. 1989, pp. 108-113.

S.A. Coulombe et al., "Ellipsometric-Scatterometry for sub-0.1 μm CD Measurements," *SPIE*, vol. 3332, pp. 282-293. 2002.

* cited by examiner

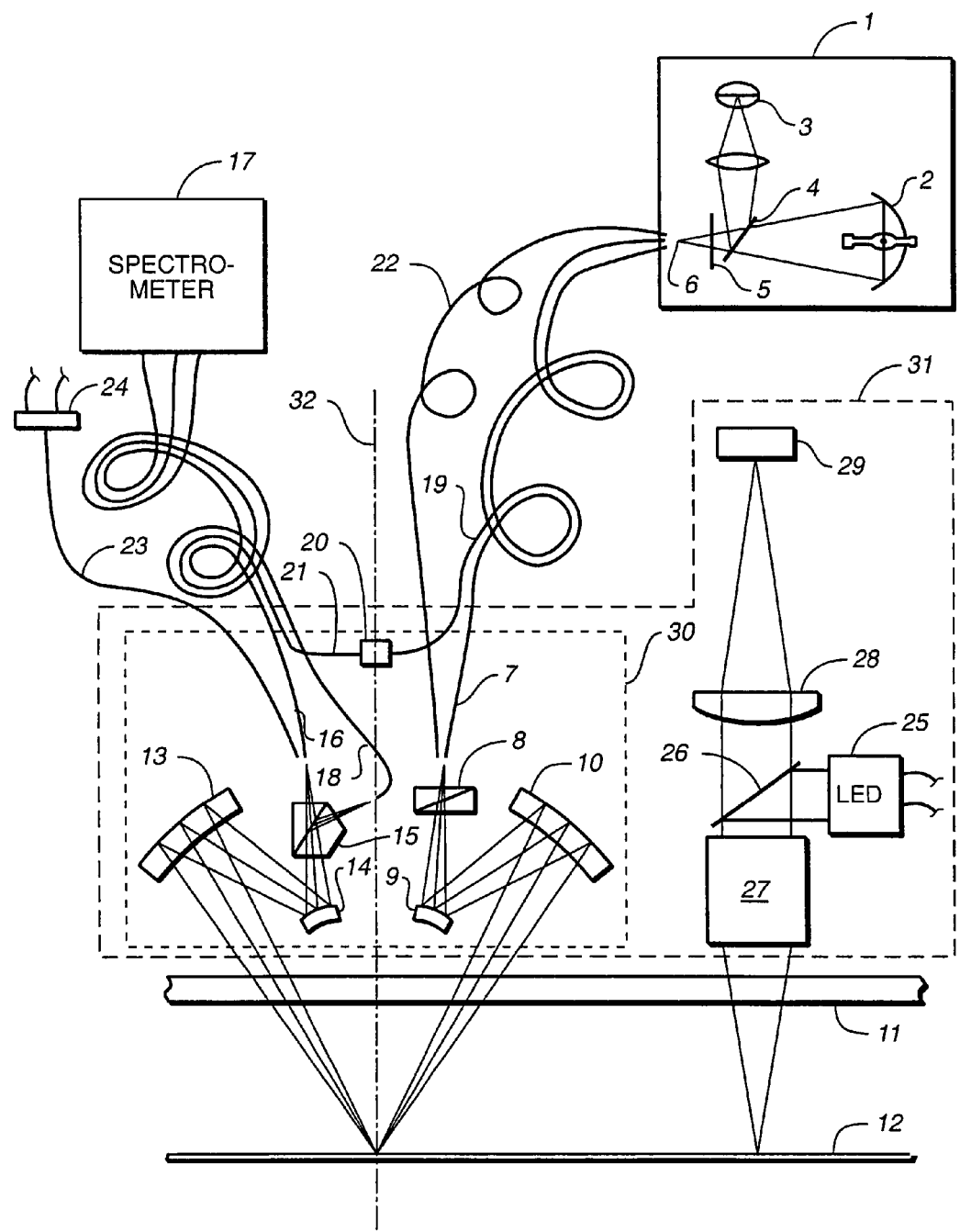
FIG._1

POLARIMETRIC SCATTEROMETRY METHODS FOR CRITICAL DIMENSION MEASUREMENTS OF PERIODIC STRUCTURES

CLAIM OF PRIORITY

This application is a continuation of Ser. No. 11/105,099, filed Apr. 13, 2005, (now U.S. Pat. No. 7,289,219), which in turn is a continuation of U.S. patent application Ser. No. 10/857,223 filed May 28, 2004 (now U.S. Pat. No. 6,909,507), which in turn is a continuation of U.S. patent application Ser. No. 10/112,138, filed Mar. 29, 2002 (now U.S. Pat. No. 6,778,273), which claims priority to U.S. Provisional Application No. 60/280,714, filed Mar. 30, 2001, all of which are incorporated herein by reference.

TECHNICAL FIELD

The present invention relates to optical measurement instruments and approaches for wafer testing during the manufacture of integrated circuits.

BACKGROUND

In the manufacture of integrated circuits, very thin lines or holes down to 100 nm or sometimes smaller are patterned into photo resist and then often transferred using an etching process into a layer of material below on a silicon wafer. It is extremely important to inspect and control the width and profile (also known as critical dimensions or CDs) of these lines or holes. Traditionally the inspection of CDs that are smaller than the wavelength of visible light has been done using large and expensive scanning electron microscopes. In many cases, however, manufacturers would like to have measurements immediately after the photoresist has been patterned or etched to have tight control of the process before it drifts out of spec. Testing the wafer early during production and controlling the fabrication steps according to the test results helps to keep production costs low and to keep yields high. Ideally the measurement tool would be integrated into the wafer track that develops the photoresist or integrated into the wafer etching tool.

In typical stand-alone instruments, the wafer is moved on a stage, while the measurement optics remain stationary. Also, when the angle of incidence on the wafer is other than zero (e.g. in ellipsometers), the wafer is preferably oriented so that the plane of incidence is perpendicular to the lines on the wafer.

An integrated CD measurement tool must be both fast and compact, and must not damage the wafer under test. The size constraints usually mean that the wafer can not be translated across its full diameter in 2 horizontal axes to measure different sites on the wafer. Hence, a portion of the test instrument must move in one or more axes to cover the wafer. The wafer might also rotate, but this is less desirable in systems without full X-Y movement that have a preferred measurement orientation with respect to certain wafer features. Furthermore, some wafer processing tools into which the present invention may be integrated require that the wafer not move so that the processing tool robot can pick up the wafer at any time. The wafer may also be loaded into the measurement tool at an arbitrary angle creating further complications for instruments that have a preferred measurement orientation with respect to certain wafer features.

One general technique that has promise for integrated CD measurements is scatterometry. This technique takes advantage of the fact that an array of small lines or holes affects the properties of the light in the zero order that is reflected (or, for transparent samples, transmitted) from such an array. Various measurable properties of the zero-order light will vary depending on the dimensions of the structure on the wafer. Often such parameters are measured versus wavelength, and in some cases, versus angle of incidence on the sample. Normal-incidence spectroscopic reflectometers show particular promise because they can be used with the wafers in any arbitrary orientation.

Typically, CD measurements have been made using instruments such as ellipsometers or reflectometers that were originally designed to measure film thickness. The data from such instruments is usually fed to a processor, which analyzes the measurements, usually by accessing a library of theoretically generated data for a range of array dimensions and film properties near those of the expected dimensions of the sample. The measured data are compared to the library and a best fit match to a data set in the library is found. The processor then outputs the corresponding dimensions.

Since there are multiple independent unknown variables that may need to be measured, such as line width, line edge slope, top film thickness, underlying film thickness, or film refractive index, it is desirable that the measurement technique measure as many multiple independent parameters as is practical.

Coulombe et al. ('Ellipsometric-Scatterometry for sub-0.1 µm CD measurements,' SPIE, Vol. 3332, p. 282-293) investigated reflectometry and ellipsometry of line gratings as a function of angle of incidence and azimuth.

One object of the present invention was to create a scatterometer for measuring CDs and possibly overlay error on periodic structures that is compact and well suited for integration into a wafer process tool.

Another object was to be able to measure on structures at different azimuth orientations.

Another object was to be able to collect as much independent data as practical from the sample. Another object was to be able to measure structures 100 nm wide or smaller.

Another object of the invention was to be able to measure structures at the optimal azimuth angle or angles regardless of the azimuth orientation of the sample.

BRIEF SUMMARY

These objects are met by a polarimetric scatterometry instrument that optically measures properties of periodic structures on a sample, using polarized light incident upon such structures. The polarized light is incident on samples at non-normal incidence (defined here as greater than 4° from perpendicular to the sample surface), and the reflected light is collected, fed into a spectrometer, and the measurements used to determine the width, profile or thickness of features associated with the illuminated periodic structures, or used to determine relative registration error between overlapping periodic structures.

The instrument includes one or more broad-spectrum light sources, e.g. a xenon lamp and a deuterium lamp, and the light from such sources may be supplied to a movable measurement head via one or more optical fibers. Likewise, light collected by the measurement head optics may be delivered to the spectrometer via one or more optical fibers. At least one polarizing element (fixed or rotatable) is situated in the beam path, with preferably a polarizer in each of the illumination and collection paths, and there may also be a polarization modulating element associated with any of the polarizers.

The measurement head may be rotated by a motor-driven mechanism to orient the plane of incidence (and collection) to different azimuth orientations θ relative to the sample. This concept of a measurement head that can be rotated as a unit to different azimuth directions can be extended to other related instruments that have a non-normal incident beam or other directional anisotropies in their optics, including for example spectroscopic ellipsometers. In addition to employing non-normal incidence and collection, ellipsometers also include rotating compensators and analyzers which, like the polarimetric scatterometer, establish a specific polarization direction to the light. The ability to rotate the measurement head allows measurements to be made on wafers at any arbitrary orientation.

The instrument, or at least the measurement head thereof, can be integrated into a wafer processing tool and wafer samples delivered to the instrument for measurement. The measurement head then moves laterally over the wafer (or the wafer moves on a stage) to specific measurement spots. Spectral reflectance measurement at each spot is then made with the polarized light at preferably three or more different azimuth angles by rotating the head. In some cases, it may be preferable for the sake of simplicity to measure the spectral reflectance at one azimuth angle, where the head is rotated so the plane of incidence on the wafer is, e.g., perpendicular to the array of periodic structures on the grating.

BRIEF DESCRIPTION OF THE DRAWINGS

FIG. 1 is a schematic side plan view of a preferred embodiment of a polarimetric scatterometer of the present invention.

DETAILED DESCRIPTION

With reference to FIG. 1, the light box 1 has a high pressure xenon lamp 2 to provide illumination between 220 and 1100 nm. It also has a deuterium lamp 3 to provide deep-UV light between 190 and 240 nm. The shorter wavelength UV light helps give better results on smaller structures. A mirror 4 can be moved into the beam path to select between the two light sources. A shutter 5 can flip into the beam to cut off all light. The shutter both protects the optics from excessive UV light and allows measurement of the detectors' background signal. The light box optics create an image 6 of the sources that is large enough to illuminate several multi-mode optical fibers 7, 19 and 22. One of these fibers 7 preferably has a core diameter of 100 microns. The output end of fiber 7 is imaged onto the wafer 12 with a demagnification of approximately 2× using curved mirrors 9 and 10. The angle of incidence on the wafer is non-normal, i.e. greater than 4° away from perpendicular to the wafer surface, and is typically anywhere between 5° and 50°. A fused silica window 11 protects the wafer 12 from particles generated from the moving optics, and also protects the optics from outgassing from the wafer.

A polarizer 8 linearly polarizes the light that is incident onto the wafer. This polarization is selected to maximize the sensitivity of the optical measurement to the parameters of the sample. In a preferred implementation, polarizer 8 allows only the S-polarized light onto the sample. In a more complex version of the invention, the polarizer 8 could be made to rotate to collect even more information about the sample. Also a rotating waveplate or electro-optic modulator (Pockels or Kerr effect based) could be placed after polarizer 8 also to collect more information on the sample's properties.

Mirrors 9 and 10 have their centers of curvature lying on or near a line between the output end of fiber 7 and its image on the wafer. These mirrors fold the light path so that the non-normal incidence does not lead to unnecessarily large footprint for the measurement head. This is desired so that the head can be integrated within a wafer process tool. Mirror 9 is a first surface convex mirror, while 10 is a concave fused silica mangin mirror. The two mirrors 9 and 10 correct the chromatic and other aberrations introduced by the window 11 and the polarizer 8 so that the image of the fiber end has near diffraction-limited quality from 190 to 1100 nm. A prescription for a representation optical design is given in an appendix A. This prescription is optimized for a particular angle of incidence, window thickness, working distance, etc. Modifications for other particular design configurations could be made by one skilled in the art.

The light reflected from the wafer is collected and imaged by mirrors 13 and 14 that are similar to mirrors 10 and 9, with their centers of curvature preferably on a line between the measurement spot on the wafer sample 12 and the input to the optical fiber 16, and correcting for any aberrations introduced by window 11 and polarizer 15. The light travels through a beamsplitting crystal polarizer 15 preferably made from alpha barium borate. The beamsplitting polarizer 15 directs images of the wafer onto the input ends of fibers 16 and 18. Fiber 16 receives S-polarized light while fiber 18 receives P-polarized light. The two fibers 16 and 18 have smaller core diameters than fiber 7 so that the measurements are not overly sensitive to focus. The diameter of the end of fibers 18 and 16 determine the geometric size of the measurement spot on the wafer, typically less than 200 μm diameter. A less complex version of this apparatus would have the beamsplitting polarizer 15 replaced by a simple polarizer so that only one polarization is detected. Another version would have polarizer 15 omitted, but that version would be less useful in measuring three-dimensional grating structures such as arrays of holes. More complex versions would replace 15 with a rotating polarizer, or fixed polarizer with rotating waveplate or electro-optic modulator.

Fibers 16 and 18 carry the two polarizations of reflected light to a multi-channel spectrometer 17 that has the capability of measuring the spectrum from each fiber simultaneously. Spectrometer 17 would have either multiple linear detector arrays or a two dimensional detector array. Multiple standard spectrometers could also be used in place of the multi-channel spectrometer 17. Alternatively, the illumination or detection could use a monochromator to serially perform measurements at various wavelengths of light.

Another fiber 19 exits the light box and closely follows the path of fiber 7 until it enters the measurement head 30. At that point it is coupled to another fiber 21 with a connector 20. Fiber 21 also closely parallels fibers 16 and 18. Fiber 21 also enters spectrometer 17, where its spectrum is used to correct for variations in the lamp intensity or transmission of the fibers versus measurement head position.

Alternatively, fiber 21 could direct its light to a photodiode (not shown) if the intensity variations are not substantially spectrally dependent. Ideally the fibers are routed so that as the measurement head 30 moves, the radius of any bends in the fiber remain constant.

The data from the spectrometer or photodiode preferably goes to a processor (not shown) where it is converted into determinations of the parameters of the structure on the wafer at the measurement spot. For example, the parameters might be the thicknesses of films, line width (critical dimension or CD), the sidewall slope of lines, etc. In one embodiment, the data is converted into spectral, absolute, polarized reflectance and compared to the spectrum library to find the best match and therefore the unknown structure parameters. There are many alternative approaches to process the data from the spectrometers to yield structure parameters. For example, the theoretical responses for comparison to the processed spectrometer data may be calculated with model parameters determined after the data is obtained. This is in distinction to comparing to library responses which are pre-computed for predetermined parameter values and stored. In yet another embodiment, parameters of structure may be calculated directly from the spectrometer data, i.e., without comparing to model results as an intermediate step.

A third fiber 22 exits the lamp house 1 and has its output end in the object plane next to the end of fiber 7. The light from fiber 22 travels through the optical system (elements 8-10 and 13-15), reflecting off the wafer and forming an image of the exit end of fiber 22 onto the entrance end of fiber 23. Fibers 22 and 23 are the same size so that the signal which is detected by a photodiode 24 is extremely sensitive to wafer focus. Autofocus is performed by scanning the measurement head 30 in Z and moving to the Z position that maximizes signal on photodiode 24. The light source for fiber 22 could also be a laser.

While the scatterometer system described above uses a remote light source and remote spectrometer (i.e., not mounted to the movable measurement head), and couples these elements to the measurement head optics via a set of optical fibers, it is also possible to mount one or both of these elements directly to the measurement head. The additional mass of such a measurement head may slow the movement of the head somewhat, but the head will still be usable, especially if the source and spectrometer are reasonably lightweight and if the motors used to move the head assembly are reasonably powerful. An advantage of direct mounting is that twisting of the optical fibers during azimuthal rotation of the measurement head can be avoided. Instead, the light from the source is directed to the sample and reflected light is collected from the sample in the normal manner, i.e. with mirrors and lenses.

The measurement head 30 is mounted to a rotating mechanism (not shown) that allows it to rotate in azimuth around the vertical axis 32. In an integrated wafer processing station, the head 30 might also be mounted to an X-Y mechanism (not shown) for providing lateral motion of the head so that it can measure different points on the wafer without having to move the wafer. Alternatively, an X-Y stage could be provided to move the wafer, especially for stand-alone measurement systems. In that case, X-Y lateral motion of the optical measurement head is unnecessary. If desired, a reduced motion stage, such as 2X,2Y stage, with or without wafer stage θ rotation, or a polar coordinate (R, θ) stage, can be used to reduce the footprint required by the wafer. Yet another configuration would have the wafer placed on a rotary stage, and the rotatable measurement head 30 mounted for radial motion. Basic construction details of rotation and X-Y drive mechanisms are well known in the art and are applicable here. The rotational axis of the measurement head 30 should coincide with the symmetry axis 32 of the measurement optics and intersect the illuminating beam at the spot on the wafer sample 12. Alternatively, a controller may have information about the relative positions of the two axes, and position the measurement head with respect to the wafer accordingly.

A complete 360° rotating range is preferred, although a 180° range would also be acceptable in many cases. A driver motor can be used, coupled to a rotatable plate on which the measurement head optics assembly is mounted. If needed, this entire unit (motor, plate, and optics) can then be mounted to the X-Y mechanism, along with the other elements within dashed box 31.

Collecting data at multiple azimuth angles on a grating structure on the wafer produces additional independent measurements that reveal more information about the structure and allows either measurement of more unknown parameters of the structure or more robust determination of a few unknowns. In the case where the wafer can not be rotated arbitrarily, the measurement head azimuth rotation also allows the plane of incidence to be aligned in the preferred perpendicular direction relative to the grating lines even when multiple azimuth angles are not needed. Furthermore, the ability to measure at two azimuth angles 180° apart can be used to reduce the sensitivity of the measurements to wafer tilt and other asymmetries in the optical system. As previously noted, this concept can be extended to related optical instruments, such as spectroscopic ellipsometers, that also have directional anisotropies in their optics. Like the preferred polarimetric scatterometer shown in the Figure, ellipsometers also have non-normal incidence and collection of a light beam. They also have specific polarization directions established by rotatable compensators and analyzers. Being able to rotate an optical measurement head in a range of azimuthal directions allows the instrument to be used with wafers or other samples at arbitrary orientations, since the head can be rotated to the desired measurement orientation.

Everything within outline 31 is mounted to the X-Y stage. The elements outside 31 may optionally be located remotely where they do not occupy the limited space available inside a wafer process tool. Within 31 there is also a viewing subsystem (elements 25-29) to view the wafer patterns and allow the exact position and orientation of the wafer to be determined relative to the X-Y stage or measurement head. A large LED 25 provides the illumination. Preferably 25 is a two color LED so that the second color can be used in case the first does not provide sufficient contrast. Alternatively, two LEDs of different colors with a dichroic beamsplitter to combine both beams could replace the single LED 25. A conventional visible beamsplitter 26 directs the illumination to an objective 27. The LED 25 is preferably placed near the entrance (or upper) pupil of 27. There are many alternative sources of illumination for a viewing system. Objective 27 and tube lens 28 form an image of the wafer on a CCD video camera 29. The position of the center of the field of view of camera 29 on the wafer is measured and calibrated (it has a known fixed offset distance) relative to the position of the image of fiber 7 on the wafer. The image from the camera 29 is fed into a pattern recognition subsystem that determines the position and angle of the wafer pattern.

A second angle of incidence can be accommodated inside measurement head 30 by having a second set of optics (not shown) with a different angle of incidence oriented in a plane separate from that of the first angle of incidence. This second angle of incidence can likewise be changed to other azimuth directions relative to the sample 12 by rotating the measurement head 30.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

APPENDIX A

GENERAL LENS DATA:

| | |
|---|---|
| Surfaces | 22 |
| Stop | 2 |
| System Aperture | Object Space NA = 0.07 |
| Glass Catalogs | schott MISC |
| Ray Aiming | Paraxial Reference, Cache On |
| X Pupil shift | 0 |
| Y Pupil shift | 0 |
| Z Pupil shift | 0 |
| Apodization | Uniform, factor = 1.00000E+000 |
| Effective Focal Length | 9.003085 (in air) |
| Effective Focal Length | 9.003085 (in image space) |
| Back Focal Length | −20.82646 |
| Total Track | 1000 |
| Image Space F/# | 0.06415 |
| Paraxial Working F/# | 19.95104 |
| Working F/# | 21.56443 |
| Image Space NA | 0.02505348 |
| Object Space NA | 0.07 |
| Stop Radius | 70.17213 |
| Paraxial Image Height | 0.03360017 |
| Paraxial Magnification | −2.800015 |
| Entrance Pupil Diameter | 140.3443 |
| Entrance Pupil Position | 1000 |
| Exit Pupil Diameter | 1.267607 |
| Exit Pupil Position | −23.90778 |
| Field Type | Object height in Millimeters |
| Maximum Field | 0.012 |
| Primary Wave | 0.55 |

APPENDIX A-continued

| | |
|---|---|
| Lens Units | Millimeters |
| Angular Magnification | 110.7159 |

Fields: 3
Field Type: Object height in Millimeters

| # | X-Value | Y-Value | Weight |
|---|---|---|---|
| 1 | 0.000000 | 0.000000 | 1.000000 |
| 2 | 0.000000 | 0.012000 | 1.000000 |
| 3 | 0.000000 | −0.012000 | 1.000000 |

Vignetting Factors:

| # | VDX | VDY | VCX | VCY | VAN |
|---|---|---|---|---|---|
| 1 | 0.000000 | 0.000000 | 0.000000 | 0.000000 | 0.000000 |
| 2 | 0.000000 | 0.000000 | 0.000000 | 0.000000 | 0.000000 |
| 3 | 0.000000 | 0.000000 | 0.000000 | 0.000000 | 0.000000 |

Wavelengths: 7
Units: Microns

| # | Value | Weight |
|---|---|---|
| 1 | 0.550000 | 1.000000 |
| 2 | 0.190000 | 1.000000 |
| 3 | 0.800000 | 1.000000 |
| 4 | 0.300000 | 1.000000 |
| 5 | 0.400000 | 1.000000 |
| 6 | 0.600000 | 1.000000 |
| 7 | 0.700000 | 1.000000 |

| Surf | Type | Comment | Radius | Thickness | Glass | Diameter | Conic |
|---|---|---|---|---|---|---|---|
| OBJ | STANDARD | | Infinity | 0 | | 0.024 | 0 |
| 1 | COORDBRK | AOI | — | 1000 | | — | — |
| STO | STANDARD | STOP | Infinity | −1000 | | 140.3443 | 0 |
| 3 | COORDBRK | | — | 0 | | — | — |
| 4 | STANDARD | WAFER AGAIN | Infinity | 15 | | 0.024 | 0 |
| 5 | STANDARD | WINDOW | Infinity | 3 | SILICA | 34.55152 | 0 |
| 6 | STANDARD | | Infinity | 39.64854 | | 38.19851 | 0 |
| 7 | COORDBRK | BACK TO OBJECT | — | −57.64854 | | — | — |
| 8 | COORDBRK | OPTIC AXIS TILT | — | 57.64854 | | — | — |
| 9 | COORDBRK | MANGIN TILT | — | 0 | | — | — |
| 10 | STANDARD | | −44.43256 | 0 | SILICA | 63.98901 | 0 |
| 11 | COORDBRK | MANGIN UNTILT | — | 2 | | — | — |
| 12 | STANDARD | | −45.89193 | −2 | MIRROR | 66.33014 | 0 |
| 13 | COORDBRK | MANGIN TILT 2 | — | 0 | | — | — |
| 14 | STANDARD | | −44.43256 | 0 | | 63.4319 | 0 |
| 15 | COORDBRK | MANGIN UNTILT 2 | — | −30.53794 | | — | — |
| 16 | STANDARD | | −12.52719 | 15.1287 | MIRROR | 9.513147 | 0 |
| 17 | COORDBRK | | — | 0 | | — | — |
| 18 | STANDARD | POLARIZER | Infinity | 3 | QUARTZ | 4 | 0 |
| 19 | STANDARD | | Infinity | 0 | | 4 | 0 |
| 20 | COORDBRK | | — | 3 | | — | — |
| 21 | COORDBRK | FIBER TILT | — | 0 | | — | — |
| IMA | STANDARD | | Infinity | | | 1.809468 | 0 |

| SURFACE DATA DETAIL: | |
|---|---|
| Surface OBJ | STANDARD |
| Surface 1 | COORDBRK |
| Comment | AOI |
| Decenter X | 0 |
| Decenter Y | 0 |
| Tilt About X | 45 |
| Tilt About Y | 0 |
| Tilt About Z | 0 |
| Order | Decenter then tilt |
| Surface STO | STANDARD |
| Comment | STOP |
| Surface 3 | COORDBRK |
| Decenter X | 0 |
| Decenter Y | 0 |
| Tilt About X | −45 |
| Tilt About Y | 0 |
| Tilt About Z | 0 |
| Order | Decenter then tilt |
| Surface 4 | STANDARD |
| Comment | WAFER AGAIN |
| Surface 5 | STANDARD |
| Comment | WINDOW |
| Coating | AR |
| Surface 6 | STANDARD |
| Coating | AR |
| Surface 7 | COORDBRK |
| Comment | BACK TO OBJECT |
| Decenter X | 0 |
| Decenter Y | 0 |
| Tilt About X | 0 |
| Tilt About Y | 0 |
| Tilt About Z | 0 |
| Order | Decenter then tilt |
| Surface 8 | COORDBRK |
| Comment | OPTIC AXIS TILT |
| Decenter X | 0 |
| Decenter Y | 0 |
| Tilt About X | 11.91948 |
| Tilt About Y | 0 |
| Tilt About Z | 0 |
| Order | Decenter then tilt |
| Surface 9 | COORDBRK |
| Comment | MANGIN TILT |
| Decenter X | 0 |
| Decenter Y | 0 |
| Tilt About X | −0.099107841 |
| Tilt About Y | 0 |
| Tilt About Z | 0 |
| Order | Decenter then tilt |
| Surface 10 | STANDARD |
| Coating | AR |
| Surface 11 | COORDBRK |
| Comment | MANGIN UNTILT |
| Decenter X | 0 |
| Decenter Y | 0 |
| Tilt About X | 0.099107841 |
| Tilt About Y | 0 |
| Tilt About Z | 0 |
| Order | Decenter then tilt |
| Surface 12 | STANDARD |
| Surface 13 | COORDBRK |
| Comment | MANGIN TILT 2 |
| Decenter X | 0 |
| Decenter Y | 0 |
| Tilt About X | −0.099107841 |
| Tilt About Y | 0 |
| Tilt About Z | 0 |
| Order | Decenter then tilt |
| Surface 14 | STANDARD |
| Coating | AR |
| Surface 15 | COORDBRK |
| Comment | MANGIN UNTILT 2 |
| Decenter X | 0 |
| Decenter Y | 0 |
| Tilt About X | 0.099107841 |
| Tilt About Y | 0 |
| Tilt About Z | 0 |
| Order | Decenter then tilt |
| Surface 16 | STANDARD |
| Surface 17 | COORDBRK |
| Decenter X | 0 |
| Decenter Y | 0 |
| Tilt About X | −10 |
| Tilt About Y | 0 |
| Tilt About Z | 0 |
| Order | Decenter then tilt |
| Surface 18 | STANDARD |
| Comment | POLARIZER |
| Aperture | Floating Aperture |
| Maximum Radius | 2 |
| Surface 19 | STANDARD |
| Aperture | Floating Aperture |
| Maximum Radius | 2 |
| Surface 20 | COORDBRK |
| Decenter X | 0 |
| Decenter Y | 0 |
| Tilt About X | 10 |
| Tilt About Y | 0 |
| Tilt About Z | 0 |
| Order | Decenter then tilt |
| Surface 21 | COORDBRK |
| Comment | FIBER TILT |
| Decenter X | 0 |
| Decenter Y | 0 |
| Tilt About X | 0 |
| Tilt About Y | 0 |
| Tilt About Z | 0 |
| Order | Decenter then tilt |
| Surface IMA | STANDARD |

| COATING DEFINITIONS: Coating AR, 1 layer(s) | | | |
|---|---|---|---|
| Material | Thickness | Absolute | Loop |
| MGF2 | 0.250000 | 0 | 0 |

What is claimed is:

1. An apparatus for evaluating a characteristic of a surface of a semiconductor wafer, comprising:

a broadband light source for generating a probe beam;

a first polarizer for polarizing the probe beam;

reflective illumination optics for focusing the probe beam to a spot on the surface at a non-normal angle of incidence;

reflective collection optics for collecting the specularly reflected probe beam;

a second polarizer for polarizing the collected reflected probe beam;

a spectrometer operable for measuring the intensity of the polarized collected specularly reflected probe beam and generate output signals as a function of wavelength; and a rotatable optical assembly for rotating the reflective optics about a rotational axis which intersects with the spot on the surface, in order to control the azimuthal angle at which the probe beam is directed to the wafer surface.

2. An apparatus as recited in claim 1, wherein said second polarizer is a polarizing beam splitter for splitting the reflected probe beam into two parts having orthogonal polarization states and wherein the spectrometer measures the intensity of both parts of the probe beam.

3. An apparatus as recited in claim 1, further including a second pair of reflective optics for focusing and collecting the probe beam, said second pair of reflective optics being positioned so that the probe beam will be directed to the surface at a second, different non-normal angle of incidence.

4. An apparatus as recited in claim 1, further including a processor for evaluating the characteristics of the wafer based on the output signals from the spectrometer.

5. An apparatus as recited in claim 4, wherein the surface includes a periodic structure and the characteristics to be evaluated include the critical dimensions of the periodic structure.

6. An apparatus as recited in claim 1, wherein said broadband light source includes two lamps generating light in two different wavelength regions.

7. An apparatus as recited in claim 6, wherein said light source includes a xenon lamp and a deuterium lamp.

8. An apparatus as recited in claim 1, further including an optical fiber for carrying the probe beam from the light source to the first polarizer.

9. An apparatus as recited in claim 8, further including an optical fiber for carrying the probe beam from the second polarizer to the spectrometer.

10. An apparatus for evaluating a characteristic of a surface of a semiconductor wafer, comprising:
    a broadband light source for generating a probe beam;
    a first polarizer for polarizing the probe beam;
    an optical assembly for coupling the polarized probe beam from the broadband light source to be incident upon a spot on the surface at a non-normal angle of incidence, the optical assembly further collecting the specularly reflected probe beam;
    a rotating mechanism coupled to the optical assembly for rotating the optical assembly about a rotational axis which intersects with the spot on the surface, in order to control the azimuthal angle direction at which the probe beam impinges upon the surface;
    a second polarizer for polarizing the collected reflected probe beam; and
    a spectrometer for measuring the intensity of the polarized collected specularly reflected probe beam and generate output signals as a function of wavelength.

11. An apparatus as recited in claim 10, further including reflective illumination optics for focusing the probe beam to a spot on the surface said non-normal angle of incidence.

12. An apparatus as recited in claim 11, further including reflective collection optics for collecting the specularly reflected probe beam.

13. An apparatus as recited in claim 10, wherein said second polarizer is a polarizing beam splitter for splitting the reflected probe beam into two parts having orthogonal polarization states and wherein the spectrometer measures the intensity of both parts of the probe beam.

14. An apparatus as recited in claim 10, further including a second pair of reflective optics for focusing and collecting the probe beam, said second pair of reflective optics being positioned so that the probe beam will be directed to the surface at a second, different non-normal angle of incidence.

15. An apparatus as recited in claim 10, further including a processor for evaluating the characteristics of the wafer based on the output signals from the spectrometer.

16. An apparatus as recited in claim 10, wherein the surface includes a periodic structure and the characteristics to be evaluated include the critical dimensions of the periodic structure.

17. An apparatus as recited in claim 10, wherein said broadband light source includes two lamps generating light in two different wavelength regions.

18. An apparatus as recited in claim 17, wherein said light source includes a xenon lamp and a deuterium lamp.

19. An apparatus as recited in claim 10, further including an optical fiber for carrying the probe beam from the light source to the first polarizer.

20. An apparatus as recited in claim 19, further including an optical fiber for carrying the probe beam from the second polarizer to the spectrometer.

* * * * *